United States Patent [19]

Stetter

[11] Patent Number: 4,818,348
[45] Date of Patent: Apr. 4, 1989

[54] METHOD AND APPARATUS FOR IDENTIFYING AND QUANTIFYING SIMPLE AND COMPLEX CHEMICALS

[75] Inventor: Joseph R. Stetter, Naperville, Ill.

[73] Assignee: Transducer Research, Inc., Naperville, Ill.

[21] Appl. No.: 53,723

[22] Filed: May 26, 1987

[51] Int. Cl.⁴ ............................................. G01N 31/00
[52] U.S. Cl. ........................................ 204/1 T; 73/23; 204/406; 204/411; 204/412; 364/497; 422/98; 436/52; 436/149; 436/150
[58] Field of Search ................ 364/497; 204/406, 411, 204/412, 1 T; 422/98; 436/52, 149, 150; 338/34; 73/23; 324/439

[56] References Cited

U.S. PATENT DOCUMENTS

| | | | |
|---|---|---|---|
| 2,149,441 | 1/1936 | Jacobson | 23/232 |
| 2,857,251 | 10/1958 | Krogh | 23/232 |
| 3,200,011 | 8/1965 | Baker | 117/217 |
| 3,540,851 | 11/1970 | Vree et al. | 23/232 |
| 3,695,848 | 10/1972 | Taguchi | 23/254 E |
| 3,713,773 | 1/1973 | Fontijn et al. | 23/232 R |
| 3,791,936 | 2/1974 | Pebler et al. | 204/1 T |
| 3,830,630 | 8/1974 | Kiefer et al. | 23/232 R |
| 3,961,248 | 6/1976 | Kawamura | 324/71 |
| 3,977,836 | 8/1976 | Matsuda et al. | 23/232 R |
| 3,997,297 | 12/1976 | Jenkins et al. | 23/232 E |
| 4,092,232 | 5/1978 | Zetter | 204/195 P |
| 4,140,106 | 2/1979 | Kirmaier | 128/2 C |
| 4,164,862 | 8/1979 | Jackson | 73/27 |
| 4,169,708 | 10/1979 | Muggli | 23/232 |
| 4,170,455 | 10/1979 | Henrie | 23/232 |
| 4,203,726 | 5/1980 | Patterson | 23/232 |
| 4,225,410 | 9/1980 | Pace | 204/195 |
| 4,266,196 | 5/1981 | Kawazoe et al. | 324/464 |
| 4,305,724 | 12/1981 | Micko | 23/232 |
| 4,315,753 | 2/1982 | Bruckenstein et al. | 23/232 E |
| 4,358,949 | 11/1982 | MacFarland et al. | 73/23 |
| 4,363,635 | 12/1982 | Hutson | 436/132 |
| 4,368,431 | 1/1983 | Rohr et al. | 324/464 |
| 4,399,684 | 8/1983 | Advani et al. | 73/1 G |
| 4,432,224 | 2/1984 | Typpo | 73/23 |
| 4,443,791 | 4/1984 | Risgin et al. | 340/634 |
| 4,443,793 | 4/1984 | Hall, Jr. | 340/634 |
| 4,457,161 | 7/1984 | Iwanaga et al. | 73/23 |
| 4,485,666 | 12/1984 | Higgins et al. | 73/23 |
| 4,542,640 | 9/1985 | Clifford | 73/23 |
| 4,596,697 | 6/1986 | Ballato | 422/98 |
| 4,638,443 | 1/1987 | Kaneyasu et al. | 364/497 |
| 4,654,127 | 3/1987 | Baker et al. | 204/1 T |

FOREIGN PATENT DOCUMENTS

| | | |
|---|---|---|
| 915458 | 11/1972 | Canada ................ 73/69 |
| 885871 | 11/1981 | U.S.S.R. . |
| 1474080 | 5/1977 | United Kingdom . |
| 2017315 | 10/1979 | United Kingdom . |
| 2047898 | 12/1980 | United Kingdom . |
| 2099588 | 12/1981 | United Kingdom . |
| 2098741 | 12/1982 | United Kingdom . |

*Primary Examiner*—G. L. Kaplan
*Attorney, Agent, or Firm*—Larson & Taylor

[57] ABSTRACT

A portable instrument for use in the field in detecting, identifying, quantifying, and monitoring gas, liquid or solid materials is disclosed. The instrument may analyze either liquids or gases depending upon the type of sensor array therein. The instrument also includes means for changing a gas, liquid or solid to a fluid material. The instrument further includes an array or small sensors which, upon exposure to the unknown material, form a pattern of electrical responses, a source of previously formed response patterns characteristic of various materials, and microprocessor means for comparing the sensor-formed response pattern with one or more previously-formed response patterns to thereby identify the material on a display. The number of responses may be increased by changing the operating voltage, temperature or other condition associated with one or more sensors to provide a plurality of responses from each of one or more of the sensors. The instrument is capable of identifying a large number of liquid and solid materials.

13 Claims, 8 Drawing Sheets

METHOD AND APPARATUS FOR IDENTIFYING AND QUANTIFYING SIMPLE AND COMPLEX CHEMICALS

This invention was made with Government support under contract number DTRS-57-85-C-00118, awarded by the Department of Transportation. The Government has certain rights in this invention.

FIELD OF THE INVENTION

The invention relates to a method and apparatus for field analysis and quantification of simple and complex chemicals. More particularly, the invention relates to a portable apparatus for performing quick and easy identification of chemical compounds present in liquid and solid materials, and a method of using this apparatus.

BACKGROUND OF THE INVENTION

This invention relates to analytical devices and more particularly to devices for analyzing the composition of liquids and solids in a sample. The invention further relates to a device capable of providing a plurality of individual electrical responses from a plurality of sensors with the responses forming a pattern charactistic of the components of a gas, vapor, liquid, a solid or a mixture thereof. The device is particularly useful when the plurality of responses exceeds the number of sensors as a result of operation of the sensors in different operating modes. More specifically, the invention relates to a portable instrument capable of being used in field locations for identifying the composition of at least one component in a solid, liquid or gas by first converting said solid, liquid or gas to a fluid and then by comparing the pattern of responses from the sensors to the fluid with one or more standard patterns stored in a memory in the instrument.

Particularly with respect to use at field locations for chemical spills and the like, devices for detecting the presence of a pollutant or other hazardous component in a material have generally been associated with one particular selected compound. Detection devices designed fpr detection of hydrogen sulfide, carbon monoxide, ammonia and the like may be considered as representative. Essentially, these devices are used to detect one or a few selected pollutants and are not designed to identify individual pollutants. When a material for analysis may contain an unknown chemical or pollutant or mixture thereof, it is usually necessary to obtain a sample of the material and send it to a remote laboratory for analysis. The time required for the transmittal of the sample and its analysis usually delays a meaningful identification of any harmful components and/or their concentration in the material for a significant time. This time delay can cause significant damage to human health, the environment and equipment.

Semi-portable versions of the more powerful laboratory gas chromatographic or infrared analyzers have been commercially introduced in recent years. These devices can respond to many chemicals and even some chemical mixtures. Besides being rather heavy, bulky, unwieldy and expensive, these instruments have certain inherent limitations. The gas chromatographic devices cannot operate in a continuous, real-time monitoring mode and require standards to be analyzed in order to identify compounds. The existing portable infrared analyzers require a delicate optical system with a rather long absorption path, which contributes to their bulk, weight and unwieldiness. Again, these cannot perform identification in the field and the identification function is only available in complex and very expensive laboratory size infrared analyzers. In addition, these instruments must usually be operated, and their results interpreted, by well-trained professionals.

An example of a device for the detection of toxic gases in a gaseous material is disclosed in a co-pending U.S. patent application Ser. No. 585,699, and now U.S. Pat. No. 4,670,405, filed on Mar. 2, 1984, which is hereby incorporated by reference.

One object of this invention is to provide a device for detecting, quantifying, and identifying one or more components of a chemically simple or complex gas, liquid or solid material.

A second object of this invention is to provide a device capable of identifying one or more components in a gas, liquid or solid material by the comparison of the response pattern of a plurality of sensors to a standard pattern.

A third object of the invention is to provide a device for identifying any of a number of unknown components or classes of compounds in a gas, liquid or solid material such as, for example, trace trichloroethane or benzene in groundwater.

Another object of the invention is to provide a device capable of providing a varied pattern of responses and thereby capable of identifying a plurality of possible materials such as gases, pure liquids, complex liquid mixtures, organic solids, inorganic solids, and mixtures of solid organic and inorganic chemicals.

An additional object of the invention is to provide a device capable of on-site analysis of a gas, liquid or solid material.

A further object of the invention is to provide a portable device for identification of gas, liquid and solid materials which is capable of being easily transported to field locations and of being operated by unskilled or semi-skilled personnel.

A further object of the present invention is to provide a portable device into which a raw, untreated chemical may be easily and automatically introduced and subsequently be identified and quantified.

Another object of the invention is to provide a portable device in which the plurality of responses obtained exceeds the number of sensors in the device.

Another object of the invention is to provide a single device capable of performing several functions including detection, identification, quantification and monitoring for a multiplicity of chemicals and chemical mixtures.

These and other objects of the invention will become apparent to one of ordinary skill in the art from the summary and detailed description which follow.

SUMMARY OF THE INVENTION

The invention relates to an instrument for detecting, quantifying, and identifying at least one component or class of chemicals. The instrument is capable of detecting, quantifying and identifying gases, liquids and solids. The instrument includes means for changing the gases, liquids and solids to an appropriate fluid. Once the gases, liquids and solids are changed to fluids they are introduced to sensing means comprising an array of sensors. The array includes at least two sensors having different electrical reponses to the fluids dependent upon the chemical interaction of the fluids with each of the sensors. The instrument also includes means for forming a response pattern from the sensing means upon exposure to the sample and means for providing a plurality of previously established response patterns. Finally, the instrument includes means for comparing the formed response pattern with at least one previously established response pattern to identify the composition of the gas, liquid or solid. A preferred embodiment of the instrument also contains a conversion means for varying the operating conditions of the device to thereby provide a plurality of responses from each sensor.

The invention also relates to a method for identifying and quantifying gases, liquids and solids comprising the steps of changing a non-gaseous sample to a gaseous material, introducing the gaseous material to an array of sensors for exposure of said gaseous material to said sensors, forming a response pattern from the responses of said sensors, and comparing the formed response pattern with a set of previously established response patterns to identify said non-gaseous materials. In this method an array of plural sensors having differing electrical responses to differing components of said gaseous material are employed. The electrical responses are dependent on the interaction of the gaseous material with each of the sensors.

The same scheme can be used for any fluid stream as long as appropriate liquid sensors are chosen for liquids and gaseous sensors are chosen for gases. The device and approach is then useful for detection, quantification, and identification of contamination in liquid streams such as groundwater, streams, lakes, and industrial effluents. Changing means may also be employed to change gases and solids to liquids for analysis.

The device is particularly useful as a small portable instrument suitable for use in the field for detecting, identifying and quantifying one or more components from a chemical spill or other emergency condition. Programming means are provided to form a response pattern from the array of sensors and compare the formed response pattern with one or more standard response patterns stored in a memory in the instrument. In one embodiment, the device includes three different heating filaments and four different electrochemical sensors with programming means capable of changing at least one operating condition for the several electrochemical sensors to identify any one of numerous gaseous components. In addition, analysis of the responses also provides data on the concentration levels of the component or components. All of these functions are self-contained in the instrument and are preprogrammed so that they may be carried out by generally unskilled personnel. In general, the instrument has a power requirement below about 2 watts and the sensors are arranged in a space less than about 8 cm × 15 cm × 8 cm. In addition, such devices can be used as part of larger devices (i.e., used as gas chromatograph or liquid chromatograph detectors) or incorporated into mobile laboratories.

DETAILED DESCRIPTION OF THE PREFERRED EMBODIMENTS

Figure 1:
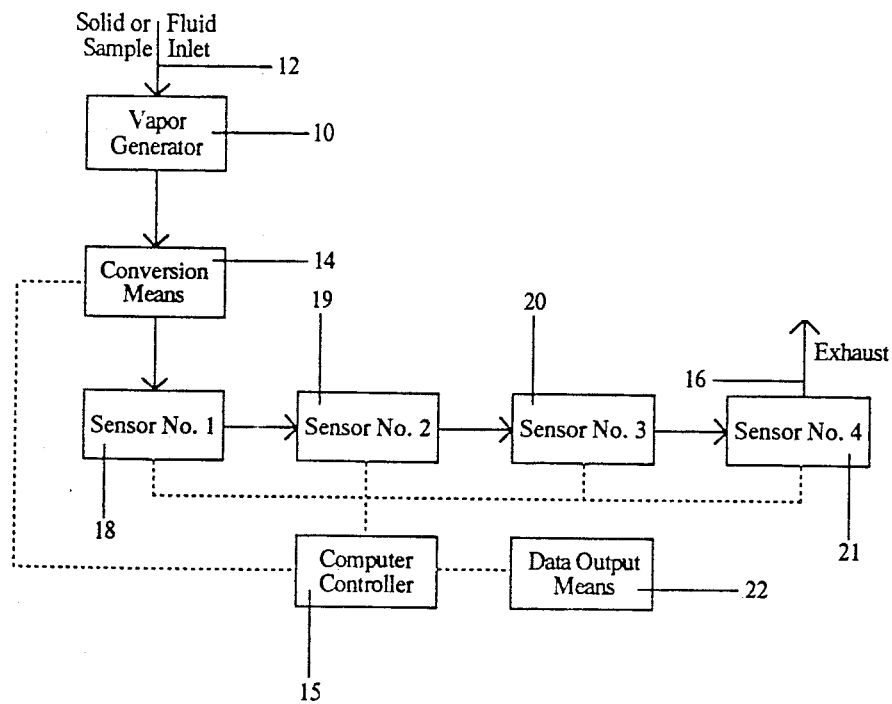
FIG. 1 is a schematic of a vapor sensor device in accordance with the invention having a sensor array with the sensors connected in series.

Referring now to FIG. 1, the vapor generator 10 includes a sample inlet 12 and an outlet 13. The outlet 13 is fluidly connected to a conversion means 14 which is controlled by a computer controller 15. From the conversion means 14 the sample is fed sequentially to sensors 18, 19, 20 and 21. The sample then passes out of the apparatus through the exhaust 16. The computer controller 15 is connected to the sensors 18–21 to both control the sensors 18–21 and acquire data from them. Connected to the computer controller 15 is a data output means 22.

Figure 2:
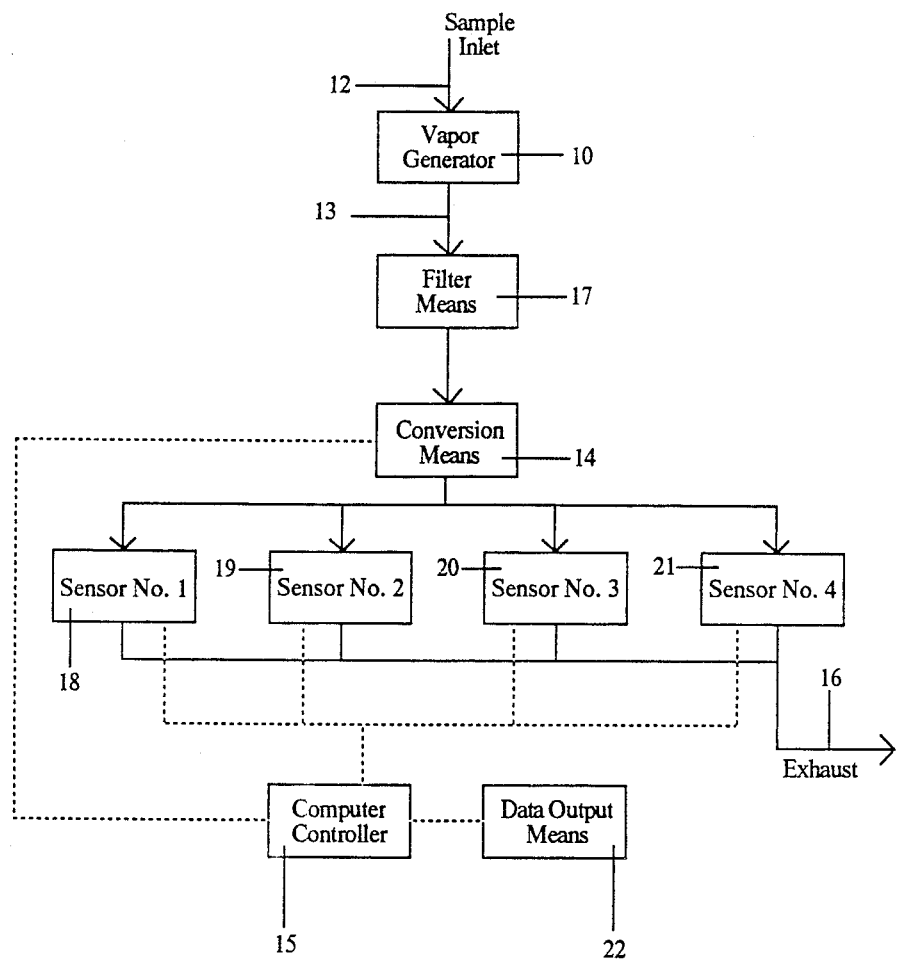
FIG. 2 is a schematic of a vapor sensor device in accordance with the invention having a sensor array with the sensors connected in parallel.

In FIG. 2, the sample is fed to vapor generator 10 having an inlet 12 and an outlet 13 and then to filter means 17. Filter 17 is provided to remove particulate materials from the sample and is only required for "dirty" samples. The resulting sample may be the initial material or its derivative or derivatives. From the filter means 17 the sample is fed to a conversion means 14 and then to sensors 18–21 arranged in parallel. After interacting with the sensors, the sample is removed via exhaust 16. Computer controller 15 is connected to the conversion means 14, the sensors 18–21 and the data output means 22.

Figure 4:
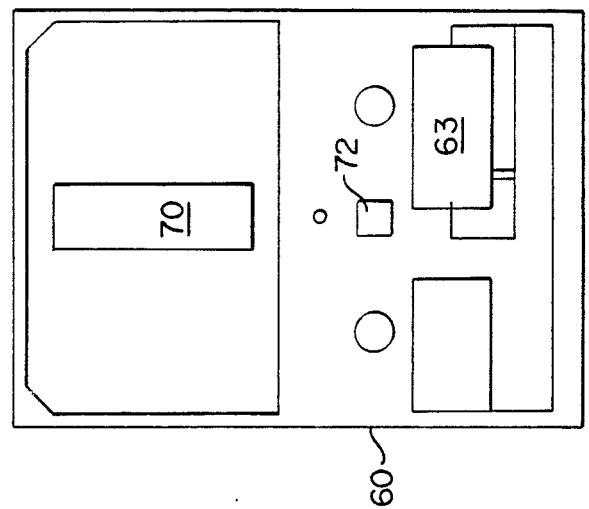
FIG. 4 is a side view of a portable instrument embodying the invention.
Figure 3:
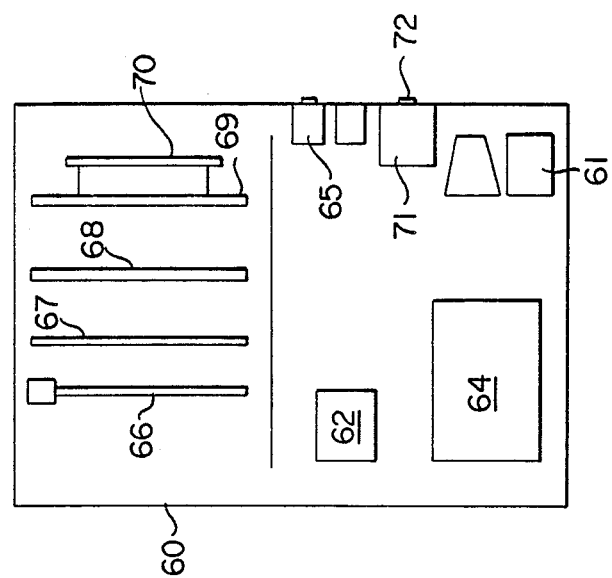
FIG. 3 represents a top view of a portable instrument embodying the invention.

FIGS. 3 and 4 provide top and side views respectively, of a portable instrument in accordance with one embodiment of the present invention. As illustrated, a housing 60 is provided which may be about 8 cm × 28 cm × 22 cm. Electrochemical cells 61 and conversion means 62 are provided as the array. The batteries 64 provide a portable power source. Filter 65 acts to remove particulate matter from the sample. Four circuit boards are also provided. Board 66 provides the central processing unit, board 67 provides the potentiometer and self-test circuits, board 68 provides the analog circuit, and board 69 provides power, alarm and display circuits. Display module 70 provides a display of data from each test. FIG. 4 illustrates a pump 63 not shown in FIG. 3. Also shown in FIGS. 3 and 4 is the vapor generator 71 having an inlet 72 which penetrates the housing 60.

Figure 5:
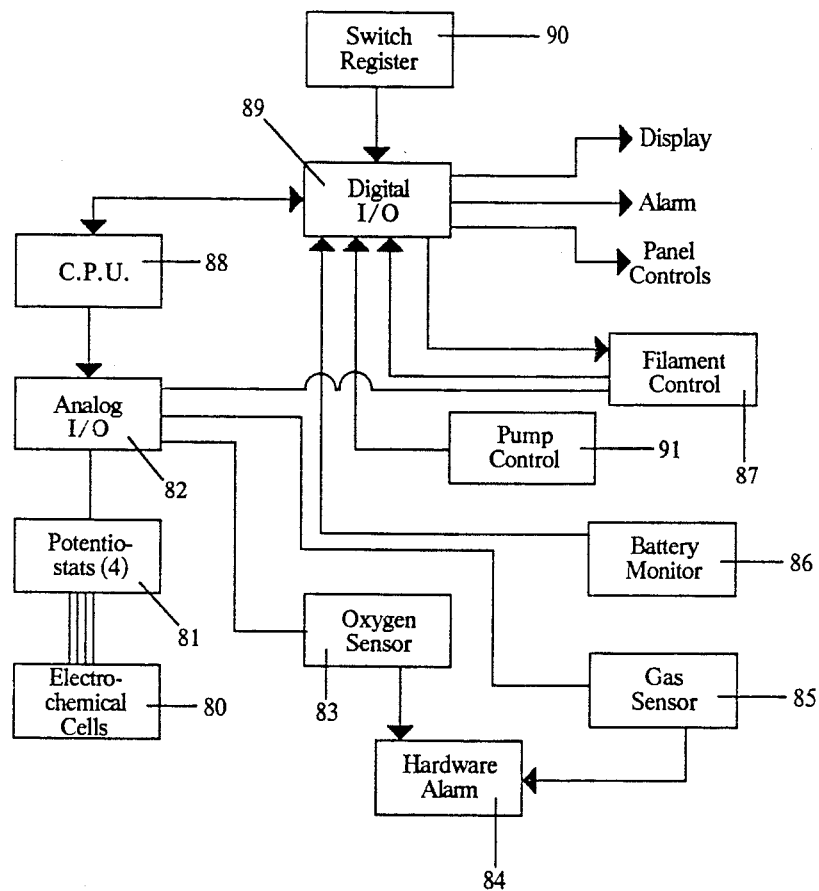
FIG. 5 is a schematic of the data generating and processing systems associated with the invention.

FIG. 5 illustrates the interconnection of the parts of the device. Electrochemical cells 80 are controlled by potentiostats 81 with the responses from the cells 80 being fed to an analog input/output 82 which also receives data and/or instructions from oxygen sensor 83, alarm B4, flammable gas sensor 85, battery monitor 86, conversion means control 87 and central processing unit 88. Digital input/output 89 is operated by switch register 90, conversion means controls 87, central processing unit 88, and pump control 91. Display and alarm signals are provided by digital input/output 89.

Figure 6:
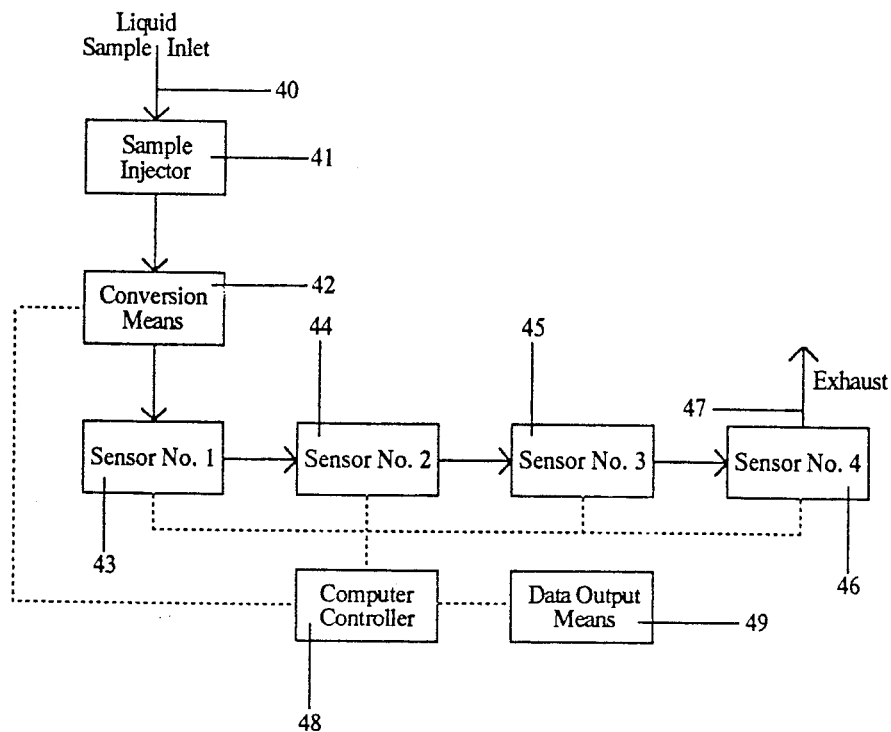
FIG. 6 is a schematic of a condensed fluid sensor array device in accordance with the invention.

Referring now to FIG. 6, the condensed fluid or liquid sensing device includes a sample inlet 40 in the sample injector 41. The sample injector 41 feeds an aliquot of sample into the conversion means 42. From there the sample passes sequentially to the liquid sensor means 43, 44, 45 and 46 and is released through exhaust 47. The conversion means 42 and liquid sensor means 43–46 are connected to a computer controller 48 having a data output means 49 attached thereto.

Figure 7:
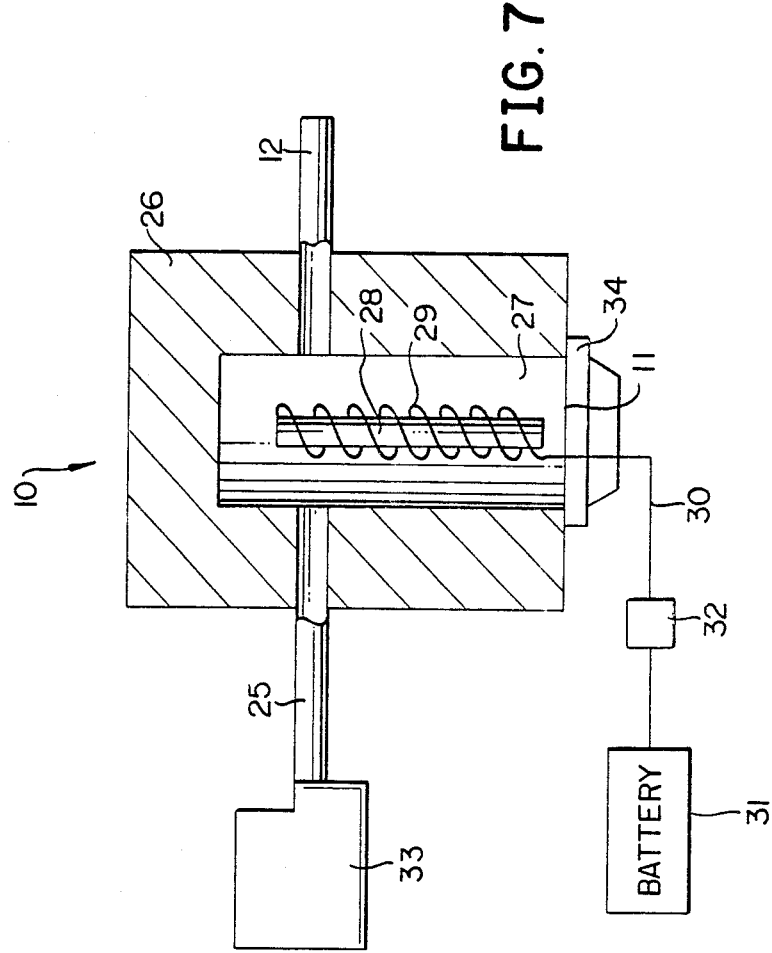
FIG. 7 is a cooss-sectional view of the vapor generator of the invention.

FIG. 7 illustrates the vapor generator 10 of the invention. The vapor generator 10 includes a block 26 having a chamber 27 therein. The chamber 27 has a sample inlet 12 and an outlet 13 fluidly connected to the sample inlet 12. Optionally the chamber 27 may also include a second inlet 25 which is connected to a pressure source 33 at the other end thereof. Shown inside the chamber 27 is the sample tube 28 with a heating filament 29 wrapped around it. The heating filament 29 is electrically connected to a battery 31 or other power source by electrical connection 30 which may include a switch 32 for manually actuating the heating filament 29. The vapor generator 10 also includes a closure member 34 for sealing the chamber 27 from the outside atmosphere.

To operate the vapor generator 10 one inserts a liquid or solid sample of material into the sample tube 28. Then the sample tube 28 is placed inside the filament 29 and sample tube 28 and filament 29 are inserted into the chamber 27 of the block 26 through the sample inlet 12. The closure member 34 is placed over the sample inlet 12 of the chamber 27 to seal the chamber 27 from the outside atmosphere. The outlet 13 of the vapor generator 10 may have a sample bag (not shown) attached thereto to collect the sample as it leaves the outlet 13. In another embodiment the vapor generator 10 is plugged directly into the inlet of a gas analyzer such that the outlet 13 of the vapor generator 10 is fluidly connected to the inlet of the gas analyzer. This causes vaporized sample to flow directly into the gas analyzer from the chamber 27 through the outlet 13.

Once the chamber 27 is sealed the filament 29 is turned on to heat the sample in the sample tube 28 and thereby vaporize the liquid or solid material into a gaseous material. This gaseous material may be caused to flow out of the outlet 13 by applying pressure to the chamber 27 through the inlet 25 from the pressure source 33. In a second embodiment a pump means (not shown) may be located downstream of the outlet 13 to generate a suction on the outlet 13 to thereby cause the gaseous material to flow out of the chamber 27 through the outlet 13. The pump means can be any suitable convection or diffusion means for introduction of the sample as well as a standard pump. Once a sufficient quantity of the gas, liquid or solid material for detection and identification has been vaporized and has left the chamber 27, the filament 29 is turned off and the sample tube 28 is removed and cleaned or replaced with another sample tube 28.

The chamber 27 serves as a location for vaporizing and holding the sample. It is heated to temperatures sufficient to vaporize a liquid or solid sample and is retained at that temperature throughout the entire identification and/or quantification process. The outlet 13 of the chamber 27 preferably includes a valve (not shown) capable of allowing passage of a predetermined aliquot of sample. Other means for metering the amount of sample leaving the chamber may be used as well. The pressure source 33 forces flow of a gaseous material to which the sensors 18–21 are nonreactive thus causing the sample to leave the chamber 27 and flow to the conversion means 14 and sensors 18–21. The chamber 27 may be large enough to house several aliquots of sample.

The present device is directed to detecting, quantifying and identifying unknown gas, liquid and solid materials in simple or complex chemicals. This is accomplished by vaporizing the liquid and solid materials and analyzing the resultant vapor using a gas sensor array, or by melting a solid or directly feeding a liquid to a liquid sensor array. The invention is particularly important for use in the field as a portable instrument for identifying one or more gases, liquids or solids from a chemical spill, fire, or other form of pollution. In addition, such devices can be used as part of larger devices such as gas and liquid choromatographs, or may be incorporated into mobile laboratories. Representative materials with which the invention provides useful results include, but are not limited to, carbon tetrachloride, gasoline, 1,6-hexanediamine, carbon monoxide, hydrogen cyanide, nitrous oxide, hydrogen sulfide, methane, benzene, toluene, cyclohexane, methanol, ethanol, diesel fuel, kerosene, mineral spirits, paint thinner, naphthalene, phenol, adipic acid, ammonium nitrate, ferric chloride hexahydrate, plant food, 1,1,2-trichloroethane and dichloromethane.

In the invention, these materials are identified by their interaction or the interaction of their derivatives with the sensors in the array. Usually, the material includes a chemically active group or groups or may be oxidized or reduced to form one or more derivatives having an active group or groups which may be identified. Through the use of a plurality of sensors in a plurality of different operating modes, more responses than sensors may be obtained. From these responses a fingerprint for each unknown compound can be developed and stored in a microprocessor. Such a fingerprint consists of a pattern formed from the responses of the sensors to the particular material being analyzed. The normalized pattern is the pattern with the largest response set equal to unity. This pattern is independent of concentration and only depends upon the identity of the chemical compounds and thus may be used as a fingerprint to positively identify a compound.

The conversion means 14 is preferably any means for varying an operational condition of the apparatus. Operational conditions include properties of the sample such as density, temperature, chemical composition and energy content, among others. Operational conditions also include characteristics of the apparatus itself such as pressure, temperature and flow rate. The conversion means 14 include but are not limited to catalysts, heat exchangers, light sources, means for causing a chemical reaction, means for causing an electrochemical reaction, pressure controllers, heaters, condensors, filters and flow controllers. Any number or type of these conversion means 14 may by incorporated into the apparatus to vary operational conditions and thereby produce a plurality of responses from each sensor.

In the invention, each of the sensors in an array is provided with a housing or other fluid containment system forming a sample chamber with the combination forming a sensing means. Means are provided for introducing a fluid sample to the sensing means which typically may be the sensing electrode of an electrochemical, especially of an amperometric, fluid sensor. The sensor array includes at least two and preferably at least three to four sensors having different electrical responses to a material or its derivative to thereby provide a plurality of different responses. Usually, the responses differ between sensors for the same material and between the same sensor for different materials. The sensors are prefrably arranged so that the first few sensors in the sequence interact with only minimal amounts of sample without significantly altering the concentration introduced into the sample chambers of the subsequent sensors. However, the interactions between the sample and the sensors represent additional conversion means and may be arranged to give maximum information about the identity and quantity of the compound. The sensors are selected and operated for optimum response to the chemicals being analyzed.

The sensor array may comprise electrochemical, catalytic or semi-conductor type sensors, or combinations of these and other types of portable, low power fluid sensors as chemiresistors, optical, piezoelectric, or pyroelectric devices, and preferably will be primarily composed of electrochemical sensors. Suitable types of electrochemical sensors include amperometric sensors having gold or platinum sensing electrodes supported on either an ion-exchange (e.g. polyfluorosulfonic acid) membrane, which also serves as the sensor electrolyte, or on a fluid-permeable electrolyte-impermeable porous polytetrafluoroethylene membrane, with the sensor electrolyte being either a strong acid, such as sulfuric acid or phosphoric acid, or a strong base, such as potassium hydroxide in aqueous solution. Sensors using other metal and non-metal electrodes in aqueous or non-aqueous solutions may also be used. In addition, a liquid sensor array may be used to identify and quantify simple and complex chemicals in liquid form. The array may also contain its own conversion means including heating filaments with exposed catalytic surfaces, chemical conversion means, thermal conversion means, conversion means using magnetic energy and photochemical conversion means. The filaments may contain catalytic materials, such as platinum, palladium, iridium, rhodium, or gold. Preferably there are at least two separate filaments, e.g., one of platinum and one of rhodium. These filaments may function to provide different degrees of oxidation of the component and also to act as sensors whose electrical current will vary with the concentration of the component.

An alternative or complementary way of increasing the number of differently selective operating modes, and thereby achieving improved selectivity is to divert the sample past one or more selective chemical filters (not shown) (e.g., cartridges containing materials having strong chemical affinity for certain compounds) by means of electronically controlled solenoid valves (not shown). Such filters may comprise activated charcoal or other adsorbants to remove organic vapors, or chemical reagents such as triethanolamine on a support to remove nitrogen dioxide. By comparing the responses of the sensor array to a sample passed through no chemical filter with the responses to the same sample past through one or more chemical filters, identification of the tested compound or compounds may be greatly facilitated.

Programming means are provided to control the sensor and automatically change response conditions in the sensor array as well as acquire appropriate signals with minimum noise. The programming means also form sensor responses into a response pattern The responses may be positive, at or about zero, or negative. These responses collectively form one or more response patterns which serve to identify the material.

Advantageously, the programming means includes means for comparing the formed response pattern with one or more previously formed patterns each being characteristic of a particular material or type of material. Preferably, the programming means also includes a memory which provides the previously formed patterns used for the comparison.

Prior to the comparison, the initial or first response pattern is converted to a second pattern in which noise and blank readings are removed. The responses are obtained by dividing the responses initially obtained by the corresponding fluid concentration and also by the average noise of each sensor corresponding to a given channel. The values in each channel are then normalized by dividing them by the highest response in the 16 channel response pattern to provide the analyzable responses.

To identify an unknown material, the programming means can first reject those candidate materials whose response patterns call for significant signals in those channels in which the tested sample gave no significant response. The programming means can then select those remaining candidate compounds whose response patterns exhibit strong responses in the same channels as in the actually observed response pattern. Finally, should this selection process yield more than one likely candidate compound, the concentrations of each of these likely candidates may be estimated by solving several simultaneous algebraic equations (developed from an analysis of the previously formed response pattern) based on a comparison of the actual response patterns of the likely candidate compounds. All of these comparisons can be performed rapidly using a microprocessor built into the instrument. In addition, once the identity of a compound or mixture is known, an accurate calibration constant can be chosen to quantify the amount of chemical species present.

The apparatus is preferably provided with microprocessor programming means in which a master program is used to select any of a plurality of functional programs which in turn may utilize one or more of certain of the other functional programs and one or more utility programs. Selection of the functional program in the preferred embodiment is by the use of an appropriate key on the face of the housing. A display is provided to show the name of the material identified by the programming means in the test period. Thus, many functions (detect, monitor, identify) are possible as well as analysis (quantification) for a multiplicity of chemical species in a single battery-operated portable, small, push-button, and simple-to-use automated device.

In one preferred embodiment, the functional programs are named the ident mode, the universal mode, the select mode, the zero mode, the calibrate mode, and the test mode. All of these programs are operated using a single keystroke by the individual operators that activate the microprocessor to run the desired program and perform the desired task. As illustrations of these modes, the following description is provided with the term "fluid" intended to refer to the material being detected.

The ident mode collects a set of data from an unknown fluid (16 data points, 4 electrochemical cells in 4 modes), subtracts a set of zero data (the signals obtained from background air) multiplies by calibration data (obtained from a calibration fluid to take into account the changing performance of cells, if any), and by treating the result as a 16-coordinate vector, compares the data to a series of pattern data sets stored in a library for various fluids (the unknown fluid data is normalized, and a euclidean distance calculation is performed between it and every pattern set). The fluid having the pattern data which is the closest to the unknown is selected as the proper identification for the fluid, and any pattern data sets having a distance from the unknown equal to or less than twice the minimum distance are selected as possible or incipient identifications. The reliability of the analysis can also be provided to the operator by inspection of the euclidean distances among compounds. The concentration of the fluid is calculated by multiplying data from the strongest channel by a concentration coefficient stored in the pattern data library, and from the results of this calculation the quantity of chemical and, therefore, the percent of immediate danger to life and health level is also determined. All of this information is displayed, and alarms are set off at the 25% and 100% immediate danger to life and health level (a beeping buzzer and flashing light-emitting diodes at 25% or greater, and a steady buzzer and light-emitting diodes at 100% and higher). The alarms can be set at any point desired. Finally, the option is provided to the operator to review the information (fluid identified, concentration, percent immediate danger to life and health, number of incipient misidentifications or reliability of the analysis, and a list of incipient misidentifications) or to exit back to the master program or a routine "main" by pressing the proper key. Exiting back to "main" shuts off any alarms and prepares the instrument for the next sample or function.

The universal mode is used to detect possibly hazardous compounds prior to their identification. A platinum or rhodium filament cycles on and off with 5 to 20 second duty cycles. The sensor responses are reported to the operator as a set of four arbitrary numbers; the alarm is triggered when any cell output exceeds a predetermined threshold.

In the "select" mode of operation, the user selects any compound pre-programmed in the library of the device and the device computer automatically selects the most sensitive response channel for the selected chemical and monitors it, reporting to the operator once per minute or so. The responses in other selected channels are examined automatically and important changes are reported to the operator.

The no signal state of the device must be measured to establish a baseline for the response of the sensors. Upon entering the zero mode, the 16 channels of information are acquired using the same routine that is called by the ident mode. Afterward, the 16-element vector is transferred to a special register. In subsequent measurements, this value is subtracted from all incoming data in the ident or universal modes.

The aging of the sensors is expected to cause gradual changes in responses over time. The calibrate mode is designed to calculate a correction factor for each channel to correct for aging. A sample of a calibration fluid such as sulfur dioxide is attached to the device. The data acquisition subroutine is called, the resulting vector is compared to that stored in the pattern library, and the ratio is stored in a special register. Each subsequent measurement in the ident mode is corrected by this ratio. If calibration is not selected, a default vector is loaded into the calibrate register, representing the state of the cells at the time that the library was compiled.

The test mode gives access to the same monitor program that was used in program development on the device. The monitor program permits these and similar functions:
(a) reading any portion of memory;
(b) changing values in RAM memory;
(c) resetting the instrument; and
(d) calling certain subroutines used for device testing.
For example, control can be used to manually adjust pump speed in both filaments.

Test mode is not intended for routine operator use. If test mode is inadvertently entered two key strokes will escape this mode. Test mode is useful in checking the device for malfunctioning components and adjusting the device for specific components.

To identify a material, a sample is first inserted into the sample tube 28 of the vapor generator 10. The sample is then vaporized by the heating filament 29 and leaves the chamber 27 through the outlet 13. The sample is then fed to the sensor array at a rate of about 0.01 to 0.5 liters per minute, and the sensors are switched into four differently selective modes at appropriate intervals (usually 30 seconds/interval). The responses of each sensor at the end of each interval are recorded in one of 16 independent data channels, and the relative magnitudes of these response signals provide the information necessary to identify the particular material giving rise to the observed signals. In addition, subsequent to identification, the largest and most responsive sensor signal can be used to quantify the compound of interest by selection of an appropriate calibration constant stored in the memory of the device. The computer-controller identifies a material based on the recorded data. The number of sensors and time required may be varied according to the complexity of the analyte. Simpler mixtures may require smaller arrays and fewer modes of operation than the more complex analytes. The device may also be operated with an increased number of sensors and a single mode of operation. The computer-controller can also set the alarm to correspond to an appropriate level associated with the short term exposure limit for immediate danger to life and health concentration of the identified material.

As covered by the above disclosure, the invention provides an analytical device useful in the field for performing the identification, quantification and monitoring of a gas, liquid or solid material by converting it to a fluid material and then analyzing it. Advantageously, the device is portable and includes a microprocessor programming means by which multiple functions may be carried out with respect to a gas, liquid or solid material depicted on a display on the device.

The following examples are included to illustrate embodiments of the present invention.

EXAMPLE 1

Figure 8:
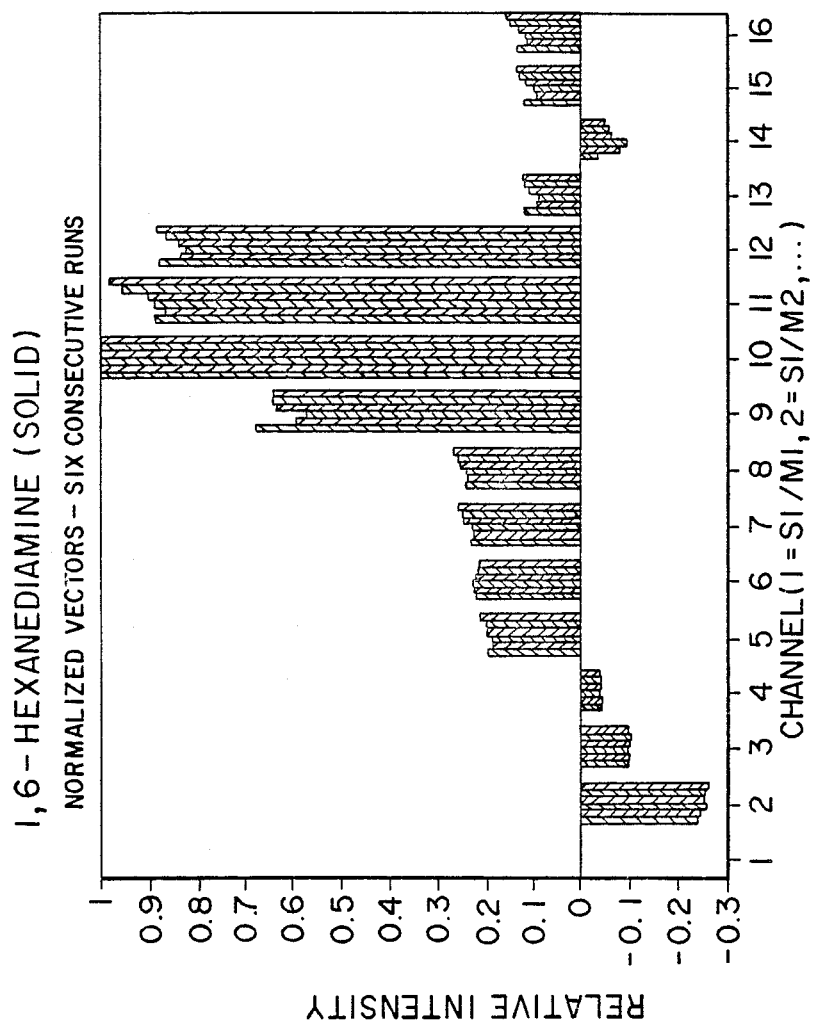
FIG. 8 is a graph of the response pattern of 1,6-hexanediamine (solid) generated by the apparatus and method of the present invention.

FIG. 8 depicts the precision of six response patterns obtained by the present apparatus for solid 1,6-hexanediamine. This fingerprint was obtained from an array of four different electrochemical gas sensors, two of which are pure gold catalytic sensing electrodes, one of which is kept at a potential of 0.8 volt and one of which is kept at a potential of 1.4 volt versus RHE (the reversible hydrogen electode). The third of the catalyst and kept at 1.2 volt versus RHE. The final sensor has a sensing electrode of platinum black bonded to a porous tetrafluoroethylene membrane, immersed in an approximately 25–30 wt. % sulfuric acid electrolyte, and potentiostated at 1.0 volt versus RHE. The array also includes two heated noble metal filaments—one of platinum and one of rhodium—that function to oxidize or partially oxidize many compounds in air. The four sensors were switched at 30 second intervals to each of the following four operating modes: (a) platinum filament heated to about 850° C.; (b) rhodium filament heated to about 900° C.; (c) rhodium filament heated to about 1000° C.; and (d) both filaments off. In these four modes the four sensors provided a total of 16 independent data channels. Six separate samples of solid 1,6-hexanediamine were analyzed by the present device and the results show the high degree of precision with which materials may be reliably fingerprinted and thereby identified.

EXAMPLE 2

Identification of Liquid Mixtures of CCl4 and Gasoline

Figure 9:
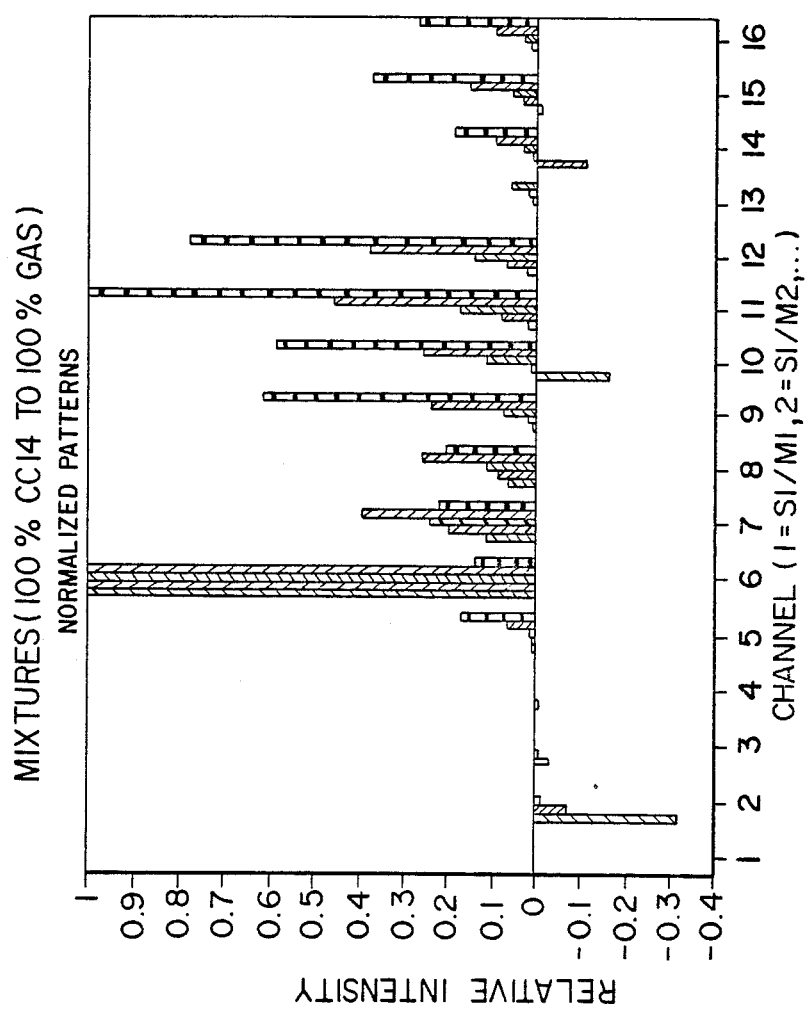
FIG. 9 is a graph of the response patterns of five different mixtures of $CCl_4$ and gasoline generated by the apparatus and method of the present invention.

The following five different mixtures of CCl4 and gasoline correspond to the five bars in each channel of FIG. 9 respectively: (1) 100% CCl4, (2) 75% CCl4 and 25% gasoline, (3) 50% CCl4 and 50% gasoline, (4) 25% CCl4 and 75% gasoline, and (5) 100% gasoline. These samples were analyzed using the same instrument under the same conditions as in Example 1. The responses shown in FIG. 9 are observed to vary from the pure CCl4 pattern to the pure gasoline pattern. Intermediate patterns have elements of both constituents and can therefore be identified and quantified.

The foregoing description of embodiments of the invention has been presented for purposes of illustration and description. It is not intended to be exhaustive or to limit the invention to the precise forms disclosed, and many modifications and variations will be obvious to one of ordinary skill in the art in light of the above teachings. The scope of the invention is to be defined by the claims appended hereto.

What is claimed is:

1. A method for identifying and quantifying at least one component of liquids and solids comprising the steps of:
    changing a non-fluid sample to a fluid material, introducing said fluid material to an array of sensors for exposure of said fluid material to said sensors, said array including plural sensors having differing electrical responses to said fluid material which are dependent on the interaction of said fluid material with each of said sensors and upon either an operational condition of at least one of said sensors or at least one property of the fluid material,
    changing an operational condition of at least one of said sensors or at least one property of the fluid material to provide a plurality of different responses from at least one of said sensors,
    forming a response pattern from the responses of said sensors, and
    comparing the formed response pattern with a set of previously established response patterns to identify at least one component of the liquids and solids.

2. A method in accordance with claim 1 wherein said step of changing a non-fluid sample comprises the steps of:
    providing a non-fluid sample to a chamber having a heating element means therein, and heating said non-fluid sample to change it to a gluid material 3. A method in acordance with claim 2 wherein a said step of introducing said fluid material to an array of sensors comprises the steps of:
    fluidly connecting said chamber with said array, and
    forcing said fluid material out of said chamber of said sensor array by introducing a fluid material into said chamber through a separate inlet.

4. A method for identifying and quantifying at least one component of gases and liquids comprising the steps of:
    changing a gaseous sample to a liquid material,
    introducing the liquid material to an array of sensors for exposure of the liquid material to said sensors, said array including plural sensors having differing electrical responses to the liquid material which are dependent on the interaction of the liquid material with each of said sensors and either at least one property of the liquid material or and operational condition of at least one of said sensors
    changing at least one property of the liquid material or an operational condition of at lest one of said sensors to provide a plurality of different responses from at least one of said sensors,
    forming a response pattern from the response of said sensors, and
    comparing the formed response pattern with a set of previously established response patterns to identify at least one component of the liquid or gaseous material.

5. A method in accordance with claim 4 wherein said step of changing a gaseous material to a liquid material comprises the steps of:
    providing a gaseous sample having a condensing means therein, and
    condensing said gaseous sample to change it to a liquid material 6. A method in accordance with claim 5 wherein said step of introducing the liquid material to an array of sensors comprises the steps of:
    fluidly connecting said chamber with said array, and
    forcing the liquid material out of said chamber to said sensor array by introducing a fluid material into said chamber through a separate inlet.

7. An instrument for identifying at least one component of gases, liquids and solids comprising,
    means for changing solids to liquids or gases, or liquids to gases, said means including at least one heating element means for vaporizing liquids and solids, a block of heat resistant material having a chamber therein, a sample container to fit within said chamber along with said heating element, means such that said container is contacted with said heating element means, and means for sealing said chamber from the atmosphere;
    sensing means including an array of sensors;
    means for introducing the liquids or gases to said sensing means, said array including at least two sensors having different electrical responses to the liquids or gases dependent on the interaction of the liquids or gases with each of said sensors and upon an operational condition of at least one of said sensors,
    means for changing an opertional condition of at least one of said sensors to provide a plurality of different responses from said at least one sensor,
    means for forming a response pattern from said sensing means upon exposure to a liquid or gaseous sample, means for providing a plurality of previously established response patterns, and means for comparing the formed response pattern with at least one previously established response pattern to identify the component of the gases, liquids and solids.

8. An instrument in accordance with claim 7 wherein said means for changing solids to liquids or gases, or liquids to gases, further comprises:

a fluid inlet connected to said chamber at one end of said inlet, and a fluid outlet connected to said chamber at one end of said outlet and to said means for introducing liquids or gases to said sensing means at a second end of said outlet.

9. An instrument for identifying at least one component of gases, liquids and solids comprising:

means for changing solids to liquids or gases, or liquids to gases, at least one condensing means for condensing gases to liquids, sensing means including an array of sensors, means for introducing the liquids or gases to said sensing means, said array including at least two sensors having different electrical responses to the liquids or gases dependent on the interaction of the liquids or gases with each of said sensors and upon an operational condition of at least one of said sensors, means for changing an operational condition of at least one of said sensors to provide a plurality of different responses from said at least one sensor, means for forming a response pattern from said sensing means upon exposure to a liquid or gas sample, means for providing a plurality of previously established response patterns, and means for comparing the formed response pattern with at least one previously established response pattern to identify the component of the gases, liquids and solids.

10. An instrument according to claim 9 wherein said sensing means comprises liquid sensors having differing electrical responses to liquids dependent on the interaction of liquids with each of said liquid sensors.

11. An instrument according to claim 10 wherein a said liquid sensors comprise at least one sensor selected from the group consisting of ultraviolet sensors, electrochemical sensors, refractive index sensors and conductimetric sensors.

12. An instrument for identifying at least one component of liquids and solids comprising:

means for changing solids to gases or liquids, or liquids to gases, said means including at least one heating element means for heating liquids and solids, a block of heat-resistant material having a chamber therein, a sample container adapted to fit within said chamber along with said heating element means such that said container is contacted with said heating element means, and means for sealing said chamber from the atmosphere, sensing means including an array of sensors, means for introducing the liquids or gases to said sensing means, said array including at least two sensors having different electrical responses to the gases or liquids dependent on the interaction of the gases or liquids with each of said sensors and upon at least one property of the gases or liquids, means for changing at least one property of the gases or liquids, means for forming a response pattern from said sensing means upon exposure to a gas or liquid sample, means for providing a plurality of previously established response patterns, and means for comparing the formed response pattern with at least one previously established response pattern to identify the component of the liquids and solids.

13. An instrument in accordance with claim 12 wherein said means for changing solids to liquids or gases or liquids to gases further comprises a fluid inlet connected to said chamber at one end of said inlet, and a fluid outlet connected to said chamber at one end of said outlet and to said means for introducing fluids to said sensing means at a second end of said outlet.

* * * * *